United States Patent
Kohl et al.

(10) Patent No.: US 7,795,432 B2
(45) Date of Patent: Sep. 14, 2010

(54) MONOFUNCTIONALIZED PERYLENETETRACARBOXYLIC ACID BISIMIDES

(75) Inventors: Christopher Kohl, Mainz (DE); Jianqiang Qu, Mannheim (DE); Klaus Müllen, Köln (DE)

(73) Assignee: Max-Planck-Gesellschaft zur Forderung der Wissenschaften e.V., Munich (DE)

( * ) Notice: Subject to any disclaimer, the term of this patent is extended or adjusted under 35 U.S.C. 154(b) by 1059 days.

(21) Appl. No.: 10/547,516

(22) PCT Filed: Feb. 27, 2004

(86) PCT No.: PCT/EP2004/001971

§ 371 (c)(1), (2), (4) Date: Aug. 21, 2006

(87) PCT Pub. No.: WO2004/076563

PCT Pub. Date: Sep. 10, 2004

(65) Prior Publication Data

US 2007/0043218 A1 Feb. 22, 2007

(30) Foreign Application Priority Data

Feb. 28, 2003 (DE) ................. 103 08 941

(51) Int. Cl.
C07D 471/02 (2006.01)
C07D 471/08 (2006.01)
(52) U.S. Cl. .......................... 546/37; 546/36
(58) Field of Classification Search ................ 546/37, 546/36
See application file for complete search history.

(56) References Cited

FOREIGN PATENT DOCUMENTS

| WO | WO99/31069 A | 6/1999 |
| WO | WO01/69254 A | 9/2001 |

OTHER PUBLICATIONS

Quante et al., "Novel Perylene-Containing Polymers"; Macromolecular Chemistry and Physics, Wiley VCH, Weinheim; vol. 197, Nov. 1996; pp. 4029-4044.

*Primary Examiner*—Charanjit S Aulakh
(74) *Attorney, Agent, or Firm*—Sutherland Asbill & Brennan LLP

(57) ABSTRACT

The invention relates to novel perylenetetracarboxylic acid bisimide derivatives with improved performance properties.

17 Claims, 1 Drawing Sheet

MONOFUNCTIONALIZED PERYLENETETRACARBOXYLIC ACID BISIMIDES

CROSS REFERENCE TO RELATED APPLICATIONS

This application claims the priority benefit of PCT/EP2004/001971 filed on Feb. 27, 2004 and German Application 103 08 941.1 filed on Feb. 28, 2003.

The invention relates to novel perylenetetracarboxylic acid bisimide derivatives having improved performance properties.

Perylenetetracarboxylic acid bisimides are known for their exceptional thermal, chemical and photophysical stability (1). They are used as dyes and pigments, for example in reprographic processes (2), fluorescent solar collectors (3), photovoltaic cells (4) and dye lasers (5). A further possible field of application is the use as labeling groups in detection processes, in particular in diagnostic or analytical processes on biological samples, including living cells. Many of these applications are based on the high fluorescence intensity of the perylene chromophore group and on the fact that the fluorescence excitation emission wavelengths of perylenetetracarboxylic acid bisimides lie at wavelengths of above 500 nm, at which signal disruptions caused by autofluorescence of cells, biological tissues or biological liquids are negligible.

However, one disadvantage of known perylenetetracarboxylic acid bisimides is that they have poor water solubility and/or weak fluorescence intensity in water (6). These disadvantages are brought about mainly by the aggregation of dye molecules in a hydrophilic environment, as a result of which the number of biological applications is limited (7).

DE-A-37 03 513 describes perylenetetracarboxylic acid bisimides which have one or more sulfonic acid radicals in the imide structure.

Quante et al. (Macromol. Chem. Phys. 197 (1996), 4029-4044) disclose perylenetetracarboxylic acid bisimides which contain sulfonic acid groups on the basic skeleton of the perylene chromophore. Further modified perylenetetracarboxylic acid bisimides are described in EP-A-0 648 817, EP-A-0 654 504, U.S. Pat. No. 4,378,302, EP-A-0 869 959, WO 97/22607 and by Zhubanov et al. (Zh. Org. Khim. 28 (1992), 1486-1488).

EP 0 896 964 discloses perylene hydrazide imides which can be used as a detection reagent for carbonyl compounds.

WO 02/14414 discloses functionalized perylenetetracarboxylic acid bisimides which are provided as initiators or/and as reaction partners for polymerization reactions.

These compounds exhibit increased fluorescence in aqueous solutions. However, it has not been possible to fully eliminate the disadvantages of the prior art, in particular the tendency to aggregate formation in aqueous solutions.

There is therefore a great need to provide novel perylenetetracarboxylic acid bisimides having improved properties, in particular with regard to the ability to couple to binding partners, to the water solubility or/and to the fluorescence intensity in water or aqueous media.

This object is achieved in accordance with the invention by providing monofunctionalized perylenetetracarboxylic acid bisimides which preferably have at least two hydrophilic groups on the basic skeleton of the perylene chromophore. These exhibit fluorescence quantum yields of up to 80% in water and can be coupled in a defined manner to binding partners, for example biomolecules.

The invention thus provides perylenetetracarboxylic acid bisimides of the structural formula (I)

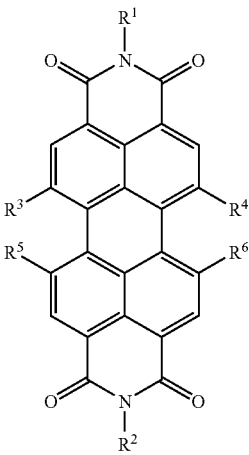

in which $R^1$ and $R^2$ are different organic radicals, one of the radicals having a group for coupling to a binding partner, and at least two of $R^3$, $R^4$, $R^5$ and $R^6$ are each independently organic radicals which contain at least one hydrophilic group.

An essential feature of the invention is that the compounds (I) are monofunctionalized compounds, i.e. compounds in which one of the two radicals $R^1$ and $R^2$ has a group for coupling to a binding partner. These coupling groups are preferably reactive functionalities which enable coupling to binding partners, in particular to amino, thiol or/and carboxyl groups in biological substances, or precursors of such reactive functionalities. Examples of suitable biological substances are nucleobases, nucleosides, nucleotides and analogs thereof, for example nucleotide derivatives for the chemical synthesis of nucleic acids, such as phosphoramidites, nucleic acids such as DNA or RNA, or else nucleic acid analogs, for instance PNA or LNA, amino acids, amino acid derivatives, peptides, polypeptides, glycoproteins, mono-, oligo- and polysaccharides, lipids, etc.

Examples of suitable reactive functionalities are active esters, maleimides, isocyanates, sulfonyl halides, carbonyl halides, in particular carbonyl chlorides, iodoacetamides, aziridines, epoxides, acyl azides and acyl nitriles. Examples of precursors of reactive functionalities are sulfonic acid groups and carboxylic acid groups which can be converted to reactive functionalities by known methods. This conversion is effected preferably after the synthesis of the basic skeleton of the compound, and it is possible if appropriate to additionally use protecting groups to prevent undesired side reactions, for example at the $R^3$, $R^4$, $R^5$ and $R^6$ positions.

The $R^1$ and $R^2$ radicals present as part of the imide structure are preferably bonded via a secondary or tertiary carbon atom to the imide nitrogen atom, although a bond via a primary carbon atom, i.e. via a $CH_2$ group, is also possible. $R^1$ and $R^2$ are more preferably secondary or tertiary aliphatic radicals or cyclic radicals having typically 3-30 carbon atoms, in particular mono- or bicyclic, aromatic or heteroaromatic radicals, for instance phenyl, pyridyl or naphthyl, which optionally bear one or more substituents. Examples of suitable substituents for aliphatic or saturated cyclic radicals are CN, $NO_2$, halogen (e.g. F, Cl, Br or I), OH, $OR^7$, $OCOR^7$, SH, $SR^7$, $SCOR^7$, $SO_2R^7$, CHO, $COR^7$, COOH, COOM, $COOR^7$, $CONH_2$, $CONHR^7$, $CON(R^7)_2$, $SO_3H$, $SO_3M$, $SO_3R^7$, $NH_2$, $NHR^7$ or $N(R^7)_2$, where M is a cation, e.g. an alkali metal ion such as sodium, potassium, etc., and $R^7$ is an optionally halogen-substituted $C_1$-$C_6$-alkyl radical. Cyclic radicals, for example aromatic or heteroaromatic radicals, may additionally be substituted by one or more $R^7$ radicals.

At least two of the $R^3$, $R^4$, $R^5$ and $R^6$ radicals bear at least one hydrophilic group. Preferably all four $R^3$, $R^4$, $R^5$ and $R^6$ radicals bear at least one hydrophilic group. The hydrophilic group may be an uncharged or charged group. Examples of suitable uncharged groups are hydroxyl groups and polyoxy-$C_2$-$C_4$-alkylene groups, in particular polyoxyethylene groups, having three or more, for example up to 50 or 100, alkylene oxide units. However, the hydrophilic group is preferably a charged group, i.e. a group which is charged in neutral media, for example at pH 7, for example a positively charged group, for instance an amino group or an ammonium group, in particular a quaternized ammonium group, or an alkylated heteroaromatic nitrogen atom, in particular an N-alkylpyridinium, N-alkylquinolinium or N-alkylisoquinolinium group, where the alkyl radical preferably has up to 6 carbon atoms and may optionally be substituted as described above. Examples of suitable negatively charged groups are sulfonic acid or carboxylic acid groups, $SO_3H$ and $COOH$, and also their $SO_3M$ and $COOM$ salts, where M is a cation, for example an alkali metal ion, for instance potassium or sodium. In addition, $R^3$, $R^4$, $R^5$ or/and $R^6$ may also contain a plurality of identically or oppositely charged groups, amphiphilic groups being formed in the latter case. Particularly preferred amphiphilic groups are heteroaromatic nitrogen atoms which are alkylated by a radical which bears a —$CO_2H$, —$SO_3H$, —$CO_2M$ or —$SO_3M$ group.

It is also preferred that at least two of the $R^3$, $R^4$, $R^5$ and $R^6$ radicals include aromatic or heteroaromatic radicals, in particular monocyclic or bicyclic radicals, for instance phenyl or pyridine.

In a particularly preferred embodiment, at least two of $R^3$, $R^4$, $R^5$ and $R^6$ are represented by the general structural formula (II)

—O—Ar (II)

in which Ar is an aromatic or heteroaromatic radical which contains at least one hydrophilic group, for example a charged group as specified above. In the case that perylenetetracarboxylic acid bisimides having negative charge carriers are used, at least one of $R^3$, $R^4$, $R^5$ and $R^6$ may have the general structural formula (III):

(III)

in which M is a cation and n is 1, 2 or 3.

In the case of the use of perylenetetracarboxylic acid bisimides having positive charge carriers, at least one of $R^3$, $R^4$, $R^5$ and $R^6$ may have the general structural formula (IV):

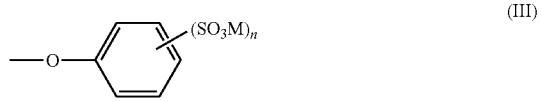

(IV)

in which $R^7$ is an optionally substituted $C_1$-$C_6$-alkyl radical, preferably $C_1$-$C_4$-alkyl radical, and Y is an anion, e.g. a halide ion. When the $R^7$ radical bears a negatively charged group as a substituent, an amphiphilic radical is obtained.

The inventive perylenetetracarboxylic acid bisimides are typically prepared from an industrially readily obtainable di- or tetra-halo-substituted perylenetetracarboxylic bisanhydride of the general structural formula (V)

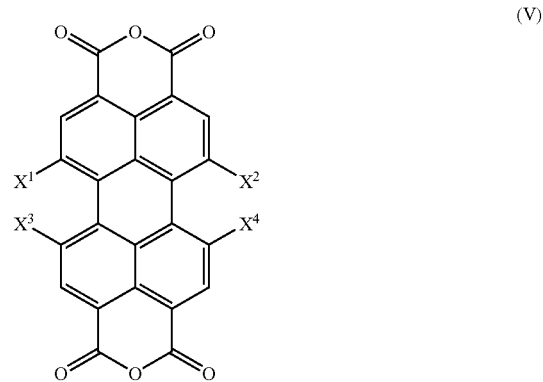

(V)

in which at least two of $X^1$, $X^2$, $X^3$ and $X^4$ are halogen, in particular Cl or Br, and the others are hydrogen, by condensation with two different primary amines, $H_2NR^1$ and $H_2NR^2$, in which $R^1$ and $R^2$ are each as defined above. Particularly preferred molar ratios of the amines are from 1 to 3 equivalents of amine based on 1 equivalent of di- or tetra-halo-substituted perylenetetracarboxylic bisanhydride, the sterically more demanding amine being used in a higher excess. Surprisingly, it has been found that a mixed substituted product is obtained in high yield in this reaction and can be removed directly from any by-products which occur, for example by column chromatography. The resulting halogen-substituted perylenetetracarboxylic acid bisimides of the general structural formula (VI)

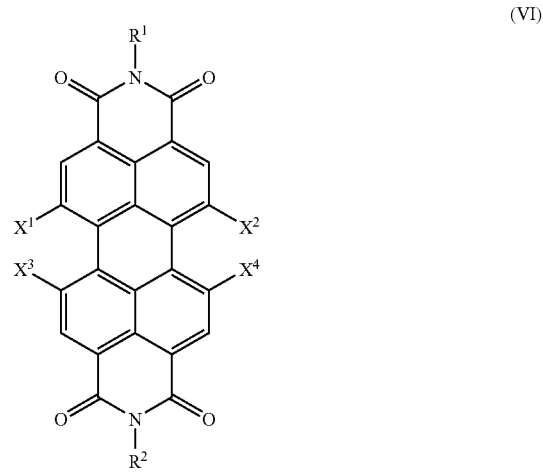

(VI)

in which at least two of $X^1$, $X^2$, $X^3$ and $X^4$ are halogen, in particular Cl or Br, and the others are hydrogen are subsequently reacted with a compound of the general structural formula (VII)

HO—Ar' (VII)

in which Ar' is an aromatic or heteroaromatic radical. This reaction forms tetra-substituted perylenetetracarboxylic acid bisimides of the general structural formula (VIIIa) or disubstituted perylenetetracarboxylic acid bisimides of the general structural formula (VIIIb):

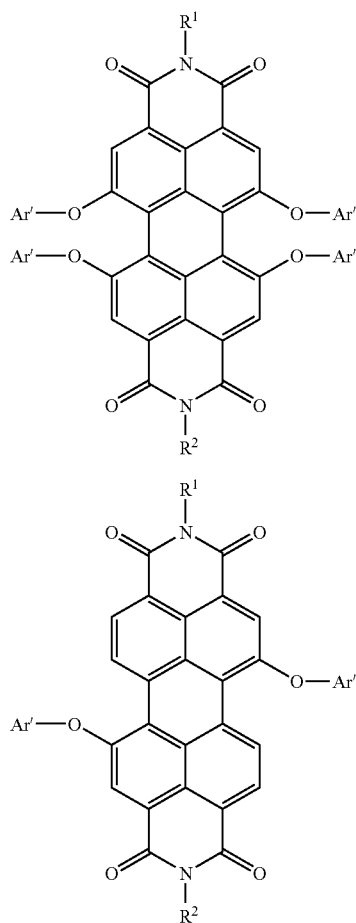

Subsequently, hydrophilic groups, as specified above, may be introduced into the aromatic or heteroaromatic Ar' radicals. For example, at least one $SO_3H$ or $SO_3M$ group may be introduced into Ar' by reaction with $H_2SO_4$ under suitable conditions. Alternatively, heteroaromatic nitrogen atoms in Ar' may be alkylated, for example by reacting with an alkyl halide, e.g. $CH_3I$, under suitable conditions.

After synthesis of the basic skeleton of the compound, the precursor of a reactive functionality in $R^1$ or $R^2$ may be converted to the reactive functionality itself.

The monofunctionalized compounds (I) may subsequently, if appropriate after removal of protecting groups, be coupled covalently to a binding partner, for example a biomolecule as specified above. The invention thus also relates to conjugates of the compounds (I) with a binding partner.

The inventive compounds may also be employed in all technical fields suitable for the use of perylenetetracarboxylic acid bisimides, for example in dye lasers, as labeling groups in analytical processes, as tracers, in scintillation counters, in fluorescence solar collectors, in liquid crystals, in cold light sources, in materials testing, as photoconductors, in photographic processes, in illumination and display elements, as semiconductors, etc.

The compounds or their conjugates, for example covalent conjugates with biomolecules such as nucleic acids, proteins, peptides, saccharides, etc., may be dissolved in liquids, for example organic or/and aqueous solvents, or in solids, for example plastics.

The present invention will be further illustrated by figures and examples.

EXAMPLES

Example 1

Figure 1:
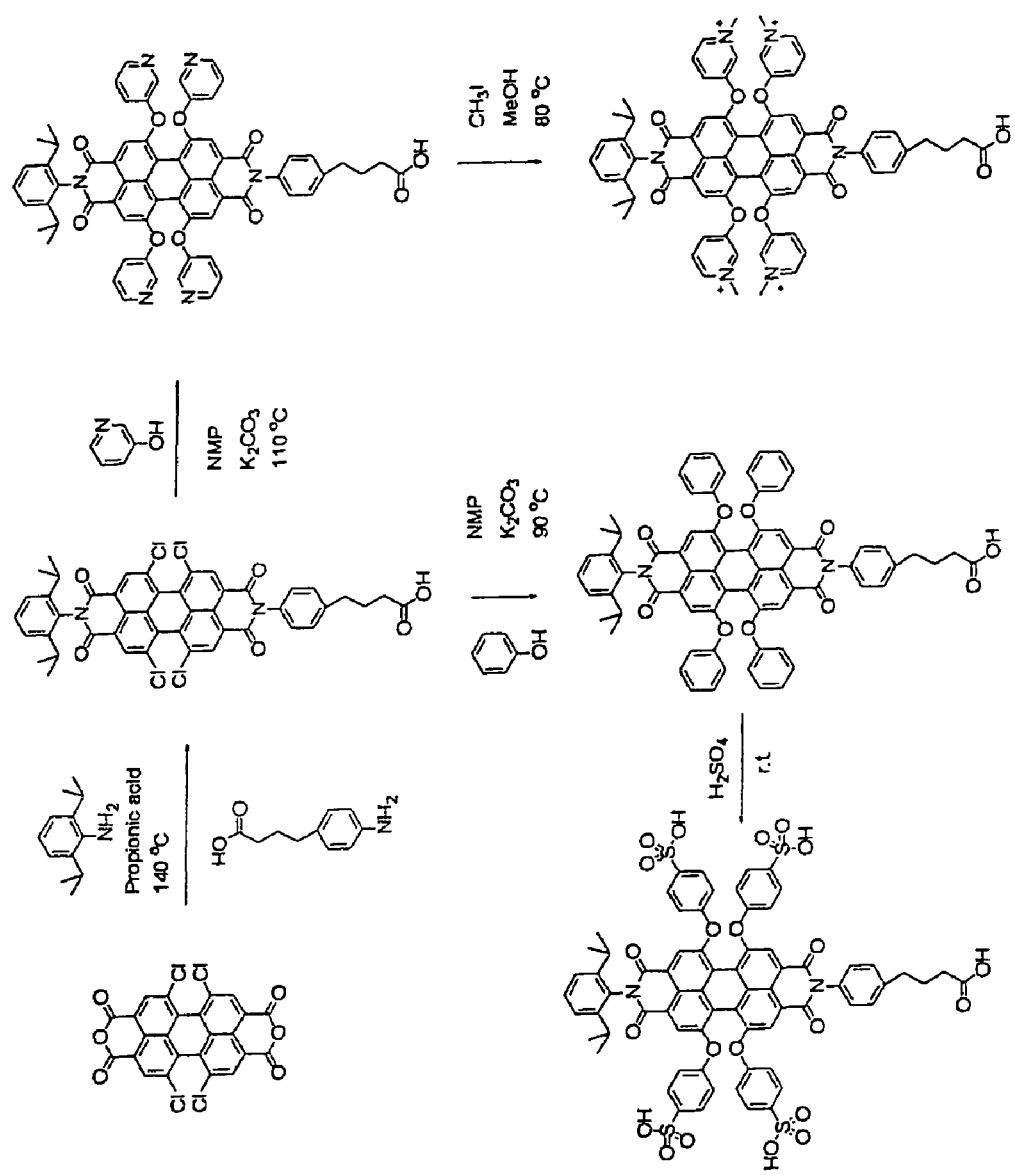
FIG. 1 shows a reaction scheme for the preparation of the tetra-substituted compounds specified in examples 1-5.

Preparation of N-(2,6-diisopropylphenyl)-N'-[(4-butyric acid)phenyl]-1,6,7,12-tetrachloroperylene-3,4:9,10-tetracarboxylic acid bisimide A mixture of 13.25 g (25 mmol) of tetrachloroperylene-3,4:9,10-tetracarboxylic bisanhydride, 13.5 g of diisopropylaniline and 5 g (28 mmol) of butyroaniline in 400 ml of propionic acid were heated to 140° C. under argon in a Schlenk flask and left at this temperature for 12 h. After cooling to room temperature, the reaction mixture was poured into water and the crude product was collected by filtration. The desired differently N,N'-substituted product was purified by column chromatography on silica gel using $CH_2Cl_2$/acetone (20:1) as the eluent.

M.P.: >300° C.; $^1$H NMR (250 MHz, $CD_2Cl_2$, 300 K): δ[ppm]: 8.76 (s, 2H), 8.74 (s, 2H), 7.54 (t, 1H), 7.45 (d, 2H), 7.38 (d, 2H), 7.28 (d, 2H), 2.80 (m, 4H), 2.73 (m, 2H); 2.09 (m, 2H), 1.16 (d, 12H). UV-Vis spectrum (chloroform) $\lambda_{max}$ (ε)=527 (46791), 494 (32499), 436 nm (12120 $M^{-1}$ $cm^{-1}$), Fluorescence spectrum (chloroform) $\lambda_{max}$=553 nm. FD mass spectrum (8 kV):m/z=849.7 (100%) [M$^+$] (Cal. 850.5)

Example 2

Preparation of N-(2,6-diisopropylphenyl)-N'-[(4-butyric acid)phenyl]-1,6,7,12-tetraphenoxyperylene-3,4:9,10-tetracarboxylic acid bisimide 8.48 g (10 mmol) of the compound prepared in example 1, 5.4 g (100 mmol) of phenol and 8.62 g (68.5 mmol) of $K_2CO_3$ were suspended under an inert gas atmosphere in 400 mmol of N-methylpyrrolidone (NMP). The reaction mixture was heated to 90° C. and stirred for 24 h. After cooling to room temperature, the mixture was poured into 5 l of aqueous HCl. The resulting precipitate was filtered, washed to neutrality and dried at 75° C. under reduced pressure. The product was further purified by chromatography on silica gel with $CH_2Cl_2$/acetone (10:1) as the eluent.

M.P.: >300° C.; $^1$H NMR (250 MHz, $CD_2Cl_2$, 300 K): δ [ppm]: 8.18 (s, 2H), 8.17 (s, 2H), 7.46 (t, 1H), 7.31 (m, 12H), 7.15 (m, 6H), 7.00 (d, 8H); 2.72 (m, 4H), 2.42 (m, 2H), 2.01 (m, 2H), 1.09 (d, 12H). UV-Vis spectrum (chloroform) $\lambda_{max}$=573, 546 nm; fluorescence spectrum (chloroform) $\lambda_{max}$32 605 nm. FD mass spectrum (8 kV):m/z=1081.8 (100%) [M$^+$] (Cal. 1081.1)

Example 3

Preparation of N-(2,6-diisopropylphenyl)-N'-[(4-butyric acid)phenyl]-1,6,7,12-tetra(4-sulfonylphenoxy)perylene-3,4:9,10-tetracarboxylic acid bisimide 0.5 g (0.46 mmol) of the compound prepared in example 2 was dissolved in 1 ml of concentrated sulfuric acid and stirred at room temperature (20° C.) for 16 h. The product was precipitated by addition of water, filtered and dried at 75° C. under reduced pressure.

M.P.: >300° C.; $^1$H NMR (250 MHz, MeOD, 300 K): δ[ppm]: 8.01 (s, 2H), 7.99 (s, 2H), 7.69 (d, 4H), 7.65 (d, 2H), 7.25 (t, 1H), 7.12 (m, 6H), 6.95 (m, 8H), 2.56 (m, 4H), 2.20 (m, 2H); 1.82 (m, 2H), 0.94 (d, 12H). UV-Vis spectrum (water) $\lambda_{max}$=575, 546 nm; fluorescence spectrum (water) $\lambda_{max}$=607 nm; MALDI-TOF mass spectrum m/z=1402.1 (100%) [M$^+$] (Cal. 1401.4).

Example 4

Preparation of N-(2,6-diisopropylphenyl)-N'-[(4-butyric acid)phenyl]-1,6,7,12-tetra(3-pyridoxy)perylene-3,4:9,10-tetracarboxylic acid bisimide 1.5 g (1.77 mmol) of the compound prepared in example 1, 1.1 g (10.7 mmol) of 3-hydroxypyridine and 1.2 g (0.8 mmol) of K$_2$CO$_3$ were dissolved in 150 ml of NMP. The reaction mixture was stirred at 110° C. under an inert gas atmosphere. After 36 h, the mixture was cooled to room temperature and neutralized with dilute hydrochloric acid. The crude product was filtered, washed with water and dried at 75° C. under reduced pressure. The resulting solid was further purified by chromatography on silica gel using CH$_2$Cl$_2$/acetone (10:1) as the eluent.

M.P.: >300° C.; $^1$H-NMR (250 MHz, CD$_2$Cl$_2$, 300 K): δ[ppm]: 8.33 (m, 8H), 8.23 (s, 2H), 8.19 (s, 2H), 7.46 (t, 1H), 7.36-7.15 (m, 14H), 2.71 (m, 4H), 2.38 (m, 2H), 1.98 (m, 2H), 1.08 (d, 12H). UV-Vis spectrum (chloroform) $\lambda_{max}$(ε)=564 (50150), 528 (32536), 446 nm (16523 M$^{-1}$ cm$^{-1}$); fluorescence spectrum (chloroform) $\lambda_{max}$=595 nm. FD mass spectrum (8 kV):m/z=1086.2 (100%) [M$^+$] (Cal. 1085.1).

Example 5

Preparation of N-(2,6-diisopropylphenyl)-N'-[(4-butyric acid)phenyl]-1,6,7,12-tetra[3-(N-methylpyridinium)oxy]perylene-3,4:9,10-tetracarboxylic acid bisimide 300 mg (0.28 mmol) of the compound prepared in example 4 were dissolved at 80° C. in 100 ml of methanol. 2 ml of methyl iodide were added to the stirred solution and the mixture was kept under reflux for 48 h. The resulting product was obtained in high purity.

M.P.: >300° C.; $^1$H NMR (250 MHz, MeOD, 300 K): δ[ppm]: 9.52-9.29 (m, 4H), 9.06 (m, 4H), 8.83-8.77 (m, 8H), 8.38 (m, 4H), 7.80 (t, 1H), 7.70 (m, 4H), 7.60 (d, 2H), 5.27 (s, 12H), 3.10 (m, 4H), 2.75 (m, 2H), 2.36 (m, 2H), 1.45 (d, 12H). UV-Vis spectrum (water) $\lambda_{max}$(ε)=547 (29974), 525 (23496), 432 nm (9456 M$^{-1}$ cm$^1$); fluorescence spectrum (water) $\lambda_{max}$=591 nm.

Example 6

Preparation of disubstituted perylenetetracarboxylic acid bisimides

Starting from N,N'-bis(2,6-diisopropylphenyl)-1,7-dibromoperylene-3,4:9,10-tetracarboxylic acid bisimide, N-(2,6-diisopropylphenyl)-N'-[(4-butyric acid)phenyl]-1,7-di(4-sulfonylphenoxy)perylene-3,4:9,10-tetracarboxylic acid bisimide was prepared according to the reaction sequence described in examples 1 to 3, and N-(2,6-diisopropylphenyl)-N'-[(4-butyric acid) phenyl]-1,7-di[3-(N-methylpyridinium)oxy]perylene-3,4:9,10-tetracarboxylic acid bisimide was prepared according to the reaction sequence described in examples 1 and 4-5.

REFERENCES (1) Y. Nagao and T. Misono, Dyes Pigm., 1984, 5, 171
  A. Rademacher, S. Merkle and H. Lanhals, Chem. Ber. 1982, 115, 2927
(2) H. O. Loutfy, A. M. Hor, P. Kazmaier and M. Tam, J. Imaging Sci., 1989, 33, 151
(3) G. Seybold and G. Wagenblast, Dyes Pigm. 1989, 11, 303
(4) L. Schmidt-Mende, A. Fechtenkötter, K. Müllen, E. Moons, R. H. Friend, J. D. MacKenzie, Science, 2001, 293, 1119
(5) R. Gvishi, R. Reisfeld and Z. Bursheim, Chem. Phys. Lett., 1993, 213, 338
(6) H. Icil, D. Uzun and N. Pasaogullari, Spectrosc. Lett., 1998, 31, 667 S. Icil. S. Demic, B. Dindar, A. O. Doroshenko and C. Timur, J. Photochem. Photobiol., 2000, 136, 15
  H. Quante, P. Schlichting, U. Rohr, Y. Geerts and K. Müllen, Macromol. Chem. Phys., 1996, 197, 4029
  W. Bauer, D. Baumgart, D. Schnaltmann, K.-P. Kreutzer and W. Zöller, EP 0 832 937 B1
  H.-A. Klok, J. Rodriguez Hernandez, S. Becker and K. Müllen, J. Polym. Sci., 2001, 39, 1572
(7) H. Han, R. J. Bennett and L. H. Hurley, Biochem. 2000, 39, 9311
  N. V. Khromov-Borisov, M. L. Indenbom and A. F. Danilov, Pharm. Chem. J. 1980, 14, 90

The invention claimed is:
1. A perylenetetracarboxylic acid bisimide of the structural formula (I)

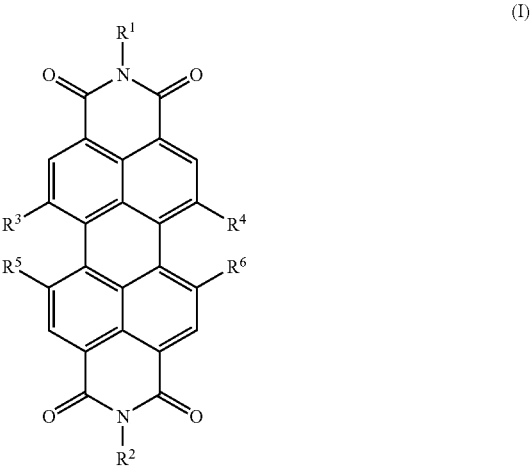

wherein R¹ and R² are different organic radicals, one of the radicals having a group for coupling to a binding partner, and at least two of R³, R⁴, R⁵ and R⁶ are each independently organic radicals which contain at least one hydrophilic group, and wherein at least one of R³, R⁴, R⁵ and R⁶ has the general structural formula (IV):

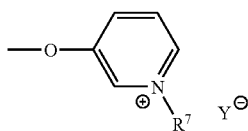

(IV)

wherein R⁷ is an optionally substituted $C_1$-$C_6$-alkyl radical and Y is an anion.

2. A compound as claimed in claim 1, wherein the coupling group is a reactive functionality for binding to amino, thiol or carboxyl groups or a precursor thereof.

3. A compound as claimed in claim 1, wherein the coupling group is an active ester, maleimide, isocyanate, sulfonyl halide, carbonyl halide, iodoacetamide, aziridine, epoxide, acyl azide, acyl nitrile or a precursor thereof.

4. A compound as claimed in claim 1, wherein R¹ or R² are secondary or tertiary aliphatic radicals or cyclic radicals.

5. A compound as claimed in claim 1, wherein R¹ or R² are aromatic or heteroaromatic radicals, in particular phenyl, pyridyl or naphthyl radicals, which optionally contain one or more substituents.

6. A compound as claimed in claim 1, wherein at least two of R³, R⁴, R⁵ and R⁶ are an organic radical which bears an uncharged hydrophilic group.

7. A compound as claimed in claim 1, wherein at least two of R³, R⁴, R⁵ and R⁶ are each independently an organic radical which bears a positively charged (in neutral media) group.

8. A compound as claimed in claim 1, wherein at least two of R³, R⁴, R⁵ and R⁶ are each independently an organic radical which bears a group selected from quaternary ammonium and N-alkylated heteroaromatic N groups such as N-alkylpyridinium, N-alkylquinolinium or N-alkylisoquinolinium groups.

9. A compound as claimed in claim 1, wherein R³, R⁴, R⁵ and R⁶ are each independently an organic radical which bears a negatively charged (in neutral media) group.

10. A compound as claimed in claim 1, wherein at least two of R³, R⁴, R⁵ and R⁶ are each independently an organic radical which bears a group selected from $SO_3H$, $COOH$, $SO_3M$ and $COOM$, wherein M is a cation.

11. A compound as claimed in claim 1, wherein R³, R⁴, R⁵ or R⁶ comprise aromatic or heteroaromatic radicals, in particular phenyl or pyridine radicals.

12. A compound as claimed in claim 1, wherein at least one of R³, R⁴, R⁵ and R⁶ has the general structural formula (II):

—O—Ar     (II)

wherein Ar is an aromatic or heteroaromatic radical which contains at least one charged group.

13. A conjugate of compounds as claimed in claim 1 with a binding partner.

14. The conjugate as claimed in claim 13, wherein the binding partner is a biomolecule.

15. A process for preparing perylenetetracarboxylic acid bisimides of claim 1, comprising the steps of:

(a) reacting halogen-substituted perylenedi- or perylenetetracarboxylic anhydrides of the general structural formula (V):

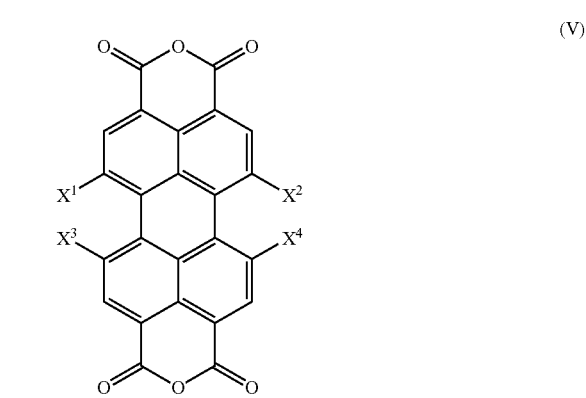

(V)

wherein at least two of X¹, X², X³ and X⁴ are halogen, in particular Cl or Br, and the others are hydrogen with a mixture of two different amines $H_2NR^1$ and $H_2NR^2$, wherein R¹ and R² are each as defined in claim 1, to give a compound of the general structural formula (VI)

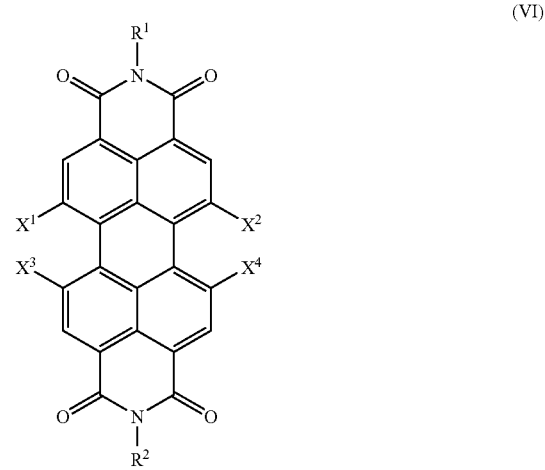

(VI)

(b) reacting the compound (VI) with a compound of the general structural formula (VII):

HO—Ar'     (VII)

wherein Ar' is an aromatic or heteroaromatic radical to give tetra-substituted perylenetetracarboxylic acid bisimides of the general structural formula (VIIIa) or to give disubstituted perylenetetracarboxylic acid bisimides of the general structural formula (VIIIb):

(VIIIa)

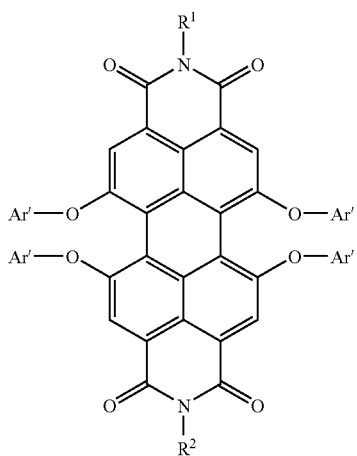

(VIIIb)

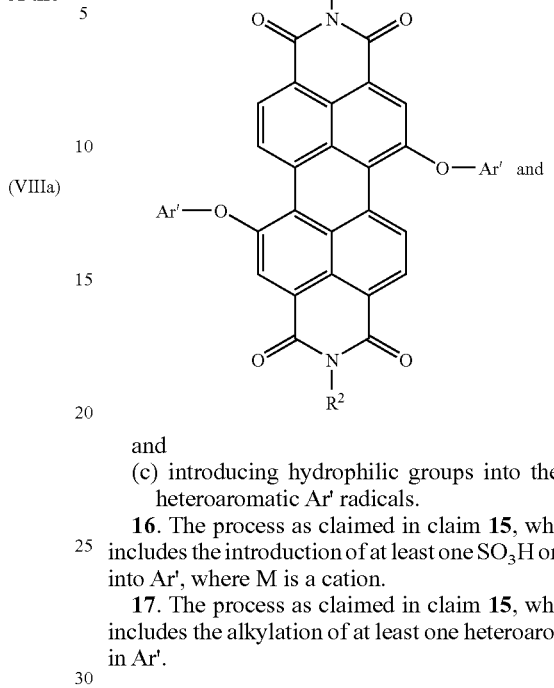

and (c) introducing hydrophilic groups into the aromatic or heteroaromatic Ar' radicals.

16. The process as claimed in claim 15, wherein step (b) includes the introduction of at least one $SO_3H$ or $SO_3M$ group into Ar', where M is a cation.

17. The process as claimed in claim 15, wherein step (b) includes the alkylation of at least one heteroaromatic N atom in Ar'.

* * * * *

UNITED STATES PATENT AND TRADEMARK OFFICE
CERTIFICATE OF CORRECTION

PATENT NO. : 7,795,432 B2  Page 1 of 1
APPLICATION NO. : 10/547516
DATED : September 14, 2010
INVENTOR(S) : Christopher Kohl et al.

It is certified that error appears in the above-identified patent and that said Letters Patent is hereby corrected as shown below:

At column 10, line 35, after "$X^1$" delete "$^{X2}$" and insert --$X^2$--.

Signed and Sealed this

Ninth Day of November, 2010

David J. Kappos
*Director of the United States Patent and Trademark Office*